US00PP35357P2

(12) United States Plant Patent
Baird et al.

(10) Patent No.: US PP35,357 P2
(45) Date of Patent: Aug. 29, 2023

(54) BERMUDAGRASS NAMED 'UCR 17-8'

(50) Latin Name: ***Cynodon dactylon* (L.) Persoon X. *Cynodon transvaalensis* Burtt-Davy.**
Varietal Denomination: UCR 17-8

(71) Applicant: The Regents of the University of California, Oakland, CA (US)

(72) Inventors: James H. Baird, Riverside, CA (US); Adam J. Lukaszewski, Riverside, CA (US); Marta Pudzianowska, Riverside, CA (US); Christian S. Bowman, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/803,476

(22) Filed: Jul. 27, 2022

(51) Int. Cl.
*A01H 5/12* (2018.01)
*A01H 6/00* (2018.01)

(52) U.S. Cl.
USPC ..... Plt./389

(58) Field of Classification Search
USPC ..... Plt./389
See application file for complete search history.

(56) References Cited

U.S. PATENT DOCUMENTS

| | | | |
|---|---|---|---|
| PP11,181 | P | 1/2000 | Riley |
| PP24,271 | P3 | 2/2014 | Wu et al. |
| PP27,392 | P2 | 11/2016 | Hanna et al. |
| PP31,695 | P3 | 4/2020 | Wu et al. |

*Primary Examiner* — Susan McCormick Ewoldt
(74) *Attorney, Agent, or Firm* — McKee, Voorhees & Sease, PLC

(57) ABSTRACT

A clonally propagated triploid turfgrass cultivar with improved winter color retention, exceptional drought resistance, and turf quality characteristics is disclosed.

2 Drawing Sheets

Botanical designation: Genus and species: *Cynodon dactylon* (L.) Persoon x. *Cynodon transvaalensis* Burtt-Davy.

Cultivar denomination: The new plant has the cultivar denomination 'UCR 17-8'.

BACKGROUND

Turfgrass offers many aesthetic, functional, and environmental benefits, especially in increasingly urbanized environments. However, declining water resources and extended drought are jeopardizing use of turfgrass in California and other arid regions. Warm-season or C4 turfgrass species including bermudagrass are much better adapted to heat, drought, and salinity compared to cool-season grasses, but they go dormant during winter months making them less desirable choices for lawns, athletic fields, and golf courses. Clear differences in winter color retention, drought tolerance, and water use efficiency exist among warm-season grasses, and even within individual species, indicating that genetic improvements are possible. Accordingly, there is a need for improved bermudagrass genotypes with emphasis on winter color retention and drought resistance for Mediterranean and arid climates.

BRIEF SUMMARY

This disclosure relates to a new and distinct cultivar of Bermudagrass designated 'UCR 17-8' and botanically known as *Cynodon dactylon* (L.) Persoon x. *Cynodon transvaalensis* Burtt-Davy. 'UCR 17-8' is a turf-type, clonally propagated, triploid bermudagrass hybrid characterized by medium-fine texture, dark blue-green color, and high quality suitable for golf course fairways. It is distinguished by very good performance under reduced irrigation and less intensive seedhead production in cooler climates.

Using conventional breeding techniques, applicants crossed bermudagrass species and planted the progeny (seed) in the greenhouse and later in the field for selection of desired traits. 'UCR 17-8' has consistently demonstrated superior winter color retention, turf quality characteristics, and exceptional drought resistance in repeated field trials across California and in other states. It is among the most drought resistant compared to commercially available cultivars. This cultivar will be useful for water savings in urban landscapes and is a step in the right direction toward eliminating the need to overseed bermudagrass in the winter months for green color.

DETAILED BOTANICAL DESCRIPTION

Figure 1:
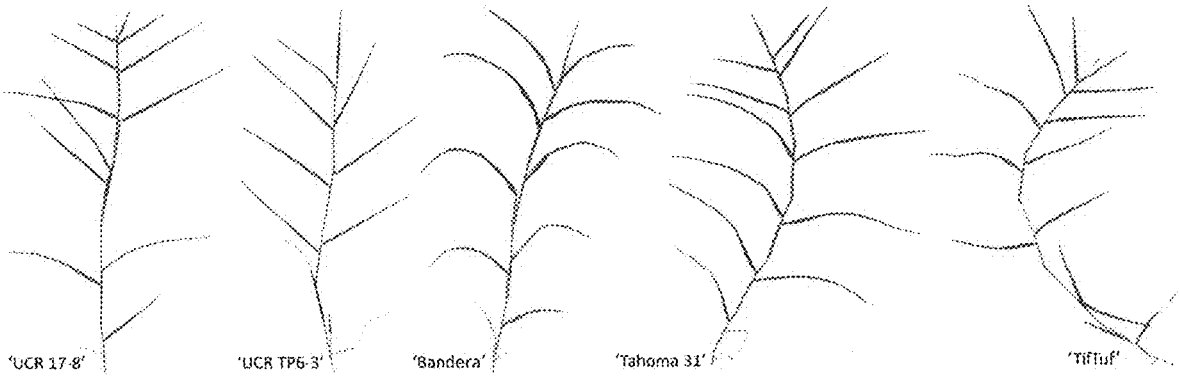
FIG. 1 is a photograph comparing shoots of 'UCR 17-8', 'UCR TP6-3', 'Bandera', 'Tahoma 31', and 'TifTuf', maintained in a greenhouse.
Figure 2:
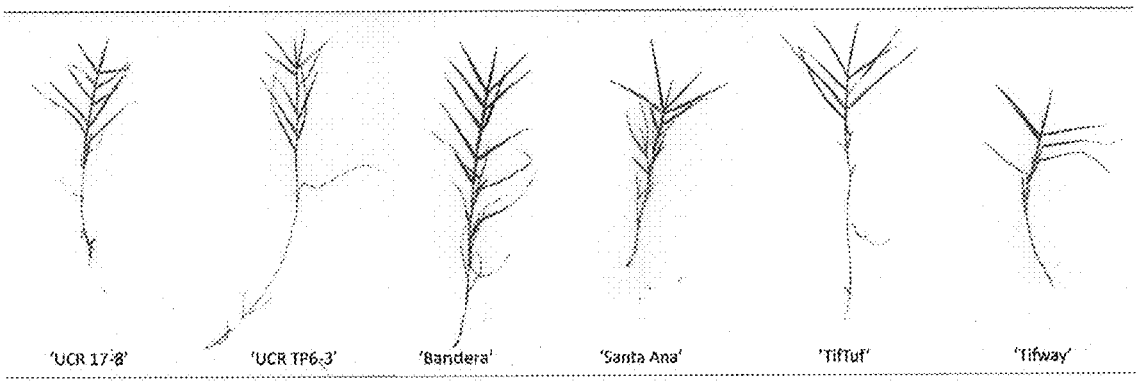
FIG. 2 is a photograph comparing shoots of 'UCR 17-8', 'UCR TP6-3', 'Bandera', 'Santa Ana', 'TifTuf' and 'Tifway', grown in the field.
Figure 3:
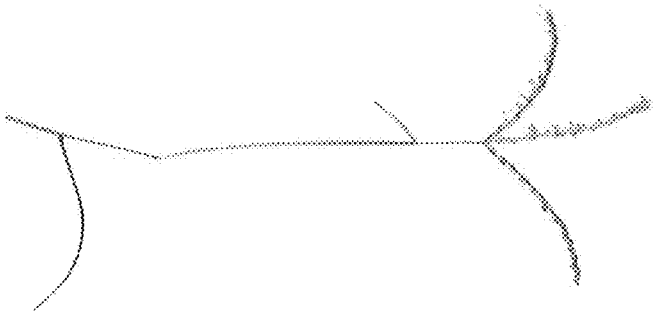
FIG. 3 is a photograph of an inflorescence of 'UCR 17-8'.
Figure 4:
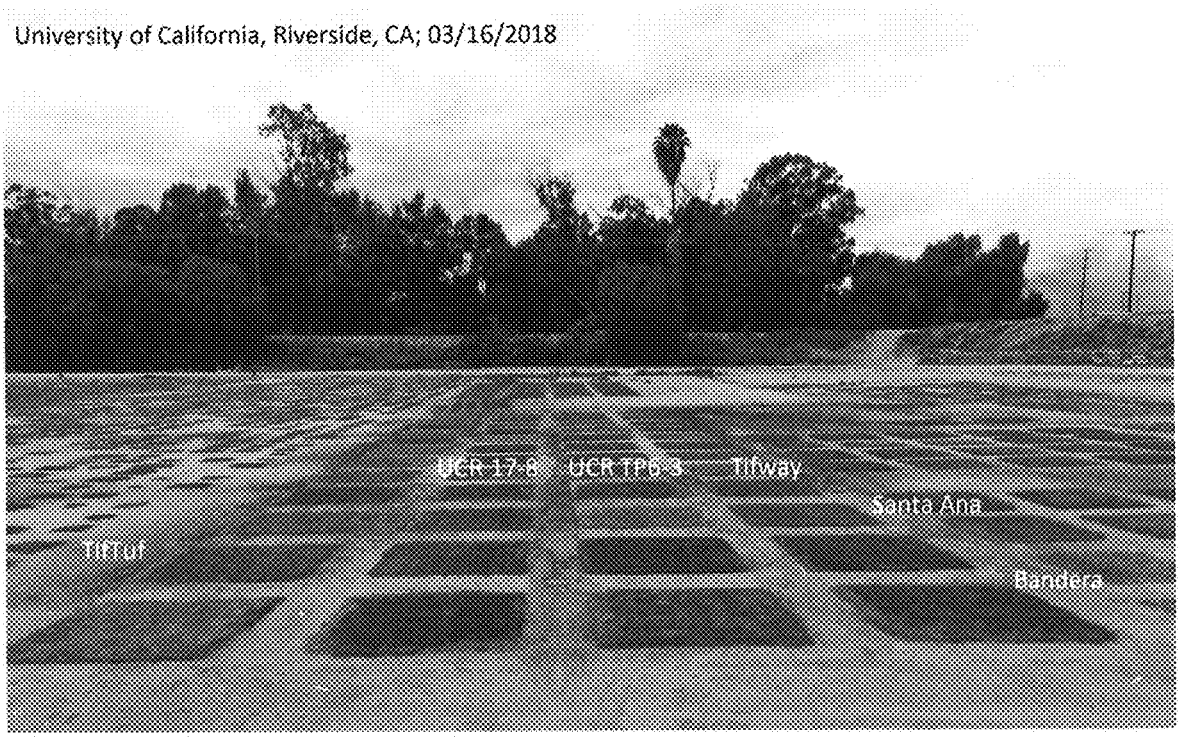
FIG. 4 is a photograph of plots of 'UCR 17-8', 'UCR TP6-3', 'Bandera', 'Santa Ana', 'TifTuf', and 'Tifway' in a replicated trial in Riverside, Calif. in March 2018.
Figure 5:
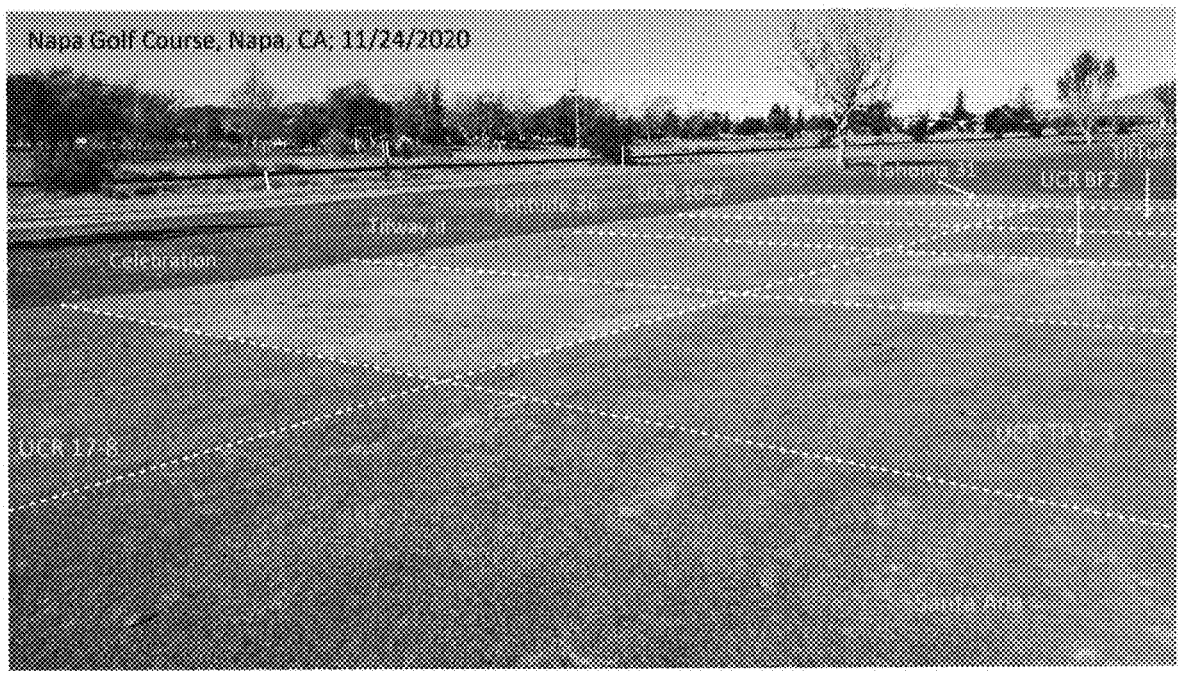
FIG. 5 is a photograph comparing fall color retention of 'UCR 17-8', 'UCR TP6-3', 'UCR BF2', 'UCR 10-9', 'Celebration', 'Latitude 36', 'Santa Ana', 'TifTuf', 'Tahoma 31' and 'Tifway II' in Napa, Calif. in November 2020.

The following is a detailed botanical description of the new cultivar of Bermudagrass, its flowers, foliage etc. as based on two to three years of continuous observations of specimens grown in greenhouse and field conditions in various locations in California.

Origin and History

'UCR 17-8' is a distinct cultivar resulting from a cross between diploid seed (female) parent *Cynodon transvaalensis* Burtt-Davy (Accession No. PI 290813) and tetraploid pollen (male) parent *Cynodon dactylon/transvaalensis* (Accession No. PI 647878). *Cynodon dactylon/transvaalensis* was initially identified as *Cynodon dactylon* and later re-identified as *Cynodon transvaalensis* in the GRIN database. Recent study of *Cynodon* spp. genetic diversity and population structure (Pudzianowska and Baird, 2020) indicate however that initial identification of PI647878 as *C. dactylon* is more probable, as it clustered together with other accessions identified as *C. dactylon*, and shows in its population composition two populations not found in most *C. transvaalensis* accessions). Crossing was achieved by detaching tillers and placing them in close proximity in a greenhouse, isolated from other bermudagrass plants. Resultant seeds were harvested in 2013 and planted in 2014 alongside 400 other hybrids in a screening nursery in Riverside, Calif. Thirty-six hybrids were selected for further evaluation in Riverside, Calif. in 2015 and in 2017 twelve were advanced for evaluation in a replicated trial in three different regions of California. In 2019, several trials were established in Riverside, Calif. and other California locations to further evaluate 'UCR 17-8' and three other superior bermudagrass hybrids.

'UCR 17-8' is sterile and must be propagated vegetatively. It has been clonally propagated in Riverside, Calif. through many seasons since 2014 and advanced generation clonal plants appear identical to the original plant in morphological phenotype and in genetic characteristics that have been measured.

Morphological Characteristics

UCR 17-8 forms a turf of medium-fine texture. The leaf blade is flat, sparsely hairy, with longer hair on adaxial surface and shorter hair on the abaxial surface. The leaf blade tapers toward the tip. Short hairs are present on the leaf margin. Vernation is folded, leaf tip is pointed, ligule is a fringe of hair, collar is narrow and continuous, and auricles—absent. The color of top and bottom surface of the leaf is dark green, with color space CIE Lab values for top surface L=8.38, a=−18.93, b=14.29, and for bottom surface L=9.48, a=−21.13, b=16.15 (values for top and bottom surface translate to RHS 135A, dark green, in The Royal Horticultural Society Colour Chart, 5$^{th}$ edition (2007)). The inflorescence is usually three spicate branches on distinct culm of approximately 72 mm of length, and CIE Lab color of L=55.03, a=−14.32, b=17.49 (RHS 138A, medium brown green).

Morphological characteristics for mature plants of 'UCR 17-8' grown in a greenhouse in Riverside, Calif. are found in Table 1 alongside 'UCR TP6-3' (U.S. Plant patent application Ser. No. 17/803,475) and three commercial cultivars 'Bandera' (not patented), 'Tahoma 31' (experimental name 'OKC 1131', U.S. Plant Pat. No. 31,695), and 'TifTuf' (experimental name 'DT-1', U.S. Plant Pat. No. 27,392). Leaf blade width, leaf blade length, internode diameter, and internode length were measured on potted plants. Measurements were collected from three replications of each cultivar with 12 subsamples of each replication in 2019. The leaf blade width of 'UCR 17-8' was found to be similar to 'UCR TP6-3', but narrower than that of 'Bandera', 'Tahoma 31', and 'Tiftuf'. The leaf blade length of 'UCR 17-8' was found to be similar to that of 'Tiftuf', shorter than that of 'UCR TP6-3', but longer than that of 'Bandera' and 'Tahoma 31'. Internode diameter of 'UCR 17-8' was similar to that of 'UCR TP6-3', 'Tahoma 31', and 'Tiftuf', but narrower than that of 'Bandera'. Internode length was similar to that of 'UCR TP6-3' and 'Tiftuf', but longer than that of 'Bandera' and 'Tahoma 31'. The color of the internodes in CIE Lab color space is L=48.68, a=−15.42, b=22.39 (RHS 138A, medium brown green).

TABLE 1

Stolon Morphology of Potted 'UCR 17-8', 'UCR TP6-3', and Three Commercial Bermudagrass Cultivars Greenhouse, Riverside, CA, 2019

| Cultivar | Leaf Blade Width (mm) | Leaf Blade Length (mm) | Internode Diameter (mm) | Internode Length (mm) |
|---|---|---|---|---|
| 'UCR 17-8' | 1.42 a | 61.31 b | 1.04 ab | 39.01 c |
| 'UCR TP6-3' | 1.50 a | 73.61 c | 0.90 a | 42.64 c |
| 'Bandera' | 1.97 b | 46.69 a | 1.23 c | 30.03 b |
| 'Tahoma 31' | 1.91 b | 50.22 a | 1.19 bc | 24.25 a |
| 'TifTuf' | 2.04 b | 60.72 b | 1.11 bc | 38.30 c |

Means followed by the same letter in a column are not significantly different at P = 0.05.

Morphological characteristics for mature plants of 'UCR 17-8' grown in field plots in Riverside, Calif. are found in Table 2 alongside 'UCR TP6-3' and four commercial cultivars 'Bandera', 'Santa Ana' (not patented), 'TifTuf', and 'Tifway' (not patented). Leaf blade width, leaf blade length, internode diameter, and internode length were measured. The field plots were established in a randomized complete block design with three replications in Riverside, Calif. in May 2017. Measurements were collected from three replications of each cultivar with 12 subsamples of each replication in 2019. The leaf blade width of 'UCR 17-8' was found to be similar to 'UCR TP6-3', 'Tiftuf', and 'Tifway', but narrower than that of 'Bandera' and 'Santa Ana'. The leaf blade length of 'UCR 17-8' was found to be similar to that of 'Bandera', 'Santa Ana', 'Tiftuf', and 'UCR TP6-3', but shorter than that of 'Tifway'. Internode diameter of 'UCR 17-8' was similar to that of 'Santa Ana', 'Tiftuf', 'Tifway', and 'UCR TP6-3', but narrower than that of 'Bandera'. Internode length was similar to that of 'UCR TP6-3', but longer than that of 'Bandera', 'Santa Ana', 'Tiftuf', and 'Tifway'.

TABLE 2

Stolon Morphology of 'UCR 17-8', 'UCR TP6-3', and Four Commercial Bermudagrass Cultivars Field Plots, Riverside, CA, 2019

| Cultivar | Leaf Blade Width (mm) | Leaf Blade Length (mm) | Internode Diameter (mm) | Internode Length (mm) |
|---|---|---|---|---|
| 'UCR 17-8' | 1.39 ab | 45.13 a | 1.06 ab | 30.06 d |
| UCR TP6-3' | 1.42 ab | 42.58 a | 1.01 a | 29.14 cd |
| 'Bandera' | 1.85 d | 42.11 a | 1.32 c | 20.43 ab |
| 'Santa Ana' | 1.63 c | 46.65 ab | 1.15 b | 17.69 a |

TABLE 2-continued

Stolon Morphology of 'UCR 17-8', 'UCR TP6-3', and Four Commercial Bermudagrass Cultivars Field Plots, Riverside, CA, 2019

| Cultivar | Leaf Blade Width (mm) | Leaf Blade Length (mm) | Internode Diameter (mm) | Internode Length (mm) |
|---|---|---|---|---|
| 'TifTuf' | 1.36 a | 47.71 ab | 0.93 a | 24.04 bc |
| 'Tifway' | 1.52 bc | 52.80 b | 1.00 a | 23.50 b |

Means followed by the same letter in a column are not significantly different at P = 0.05.

A genetic screen was performed on a population of bermudagrass genotypes, which included 'UCR 17-8', 'UCR TP6-3', 'Bandera', 'Santa Ana', 'Tifway', 'Celebration' (also known as 'Riley's Super Sport', U.S. Plant Pat. No. 11,181), and 'Latitude 36' (U.S. Plant Pat. No. 24,271), using a genotype-by-sequencing platform called Diversity Arrays Technology sequencing (DArTseq). Results are presented in Table 3. This genetic screen identified 6904 single nucleotide polymorphisms (SNP) that were found to be significantly informative when analyzing the genetic markers generated from the DArTseq data. Analysis of genetic markers was performed in R using the following packages: 'dartR', 'StAMPP', 'Rphylip', 'strataG', and 'ParallelStructure'. 'UCR 17-8' was found to be closely related with 'UCR TP6-3', with five markers differentiating between them, but distantly related to 'Bandera' (109 differentiating markers), 'Santa Ana' (131), 'Tifway' (61), 'Celebration' (287), and 'Latitude 36' (253). These numbers are indicative of genetic differences between the listed accessions, and suggest a quantifiable difference between 'UCR 17-8' and current commercial cultivars.

TABLE 3

Number of Single Nucleotide Polymorphism (SNP) Markers Differentiating 'UCR 17-8' From Other Bermudagrass Cultivars

| | Cultivar | | | | | | |
|---|---|---|---|---|---|---|---|
| Cultivar | 'UCR 17-8' | 'UCR TP6-3' | 'Bandera' | 'Santa Ana' | 'Tifway' | 'Celebration' | 'Latitude 36' |
| 'UCR 17-8' | — | | | | | | |
| 'UCRTP6-3' | 5 | — | | | | | |
| 'Bandera' | 109 | 104 | — | | | | |
| 'Santa Ana' | 131 | 126 | 26 | — | | | |
| 'Tifway' | 61 | 56 | 58 | 70 | — | | |
| 'Celebration' | 287 | 282 | 178 | 156 | 226 | — | |
| 'Latitude 36' | 253 | 249 | 144 | 122 | 192 | 34 | — |

Performance

'UCR 17-8' was advanced for further evaluation after several years of observations in the nursery and non-replicated test plots, based on good overall quality and performance under regular irrigation and drought.

In 2017, replicated trials were performed in three locations: Thermal, Calif., Fairfax, Calif., and Riverside, Calif. Establishment (% ground cover), visual turfgrass quality in the summer and in the winter (1-9; 9=best), winter color retention (1-9; 9=highest), Normalized Difference Vegetation Index (NDVI, 0-1), Dark Green Color Index (DGCI, 0-0.666) using Digital Image Analysis (DIA), and seedhead production (1-9; 1=no seedheads) were evaluated from 2017 to 2019. Comparison of 'UCR 17-8' with commercial checks ('Bandera', 'Santa Ana', 'TifTuf', 'Tifway') and 'UCR TP6-3' is presented in Tables 4, 5, and 6. The summer quality of 'UCR 17-8' at all three locations was at least acceptable. It was comparable to 'Tifway', 'TifTuf' and 'Santa Ana' in Riverside, Calif., to 'Tifway', 'Santa Ana' and 'UCR TP6-3' in Thermal, Calif., and to 'Tifway', 'TifTuf' and 'UCR TP6-3' in Fairfax, Calif. In Riverside, Calif. and Thermal, Calif., 'UCR 17-8' showed good winter quality: comparable to 'UCR TP6-3', 'Tifway' and 'TifTuf' in Riverside, Calif., and to 'UCR TP6-3' in Thermal, Calif. Winter quality of 'UCR 17-8' in these two locations was higher than the remaining cultivars in this trial. Winter color retention of 'UCR 17-8' was the highest among evaluated entries in Thermal, Calif. In Riverside, Calif., its winter color retention was higher than 'Bandera' and 'Santa Ana', and slightly lower than, but comparable to, other cultivars. In Fairfax, Calif., it was lower than 'TifTuf' and higher than 'Tifway', but overall not significantly different from all evaluated entries. Seedhead production depended on the location. In Fairfax, Calif., 'UCR 17-8' produced significantly fewer seedheads than 'TifTuf', but was comparable to other entries. In Riverside, Calif., seedhead production of 'UCR 17-8' was the lowest, comparable to 'Tifway', while in Thermal, Calif. it was high, similar to seedhead production of 'Santa Ana'.

TABLE 4

Thermal, CA 2017-2019

| | Turfgrass Quality | | Winter Color | NDVI | |
|---|---|---|---|---|---|
| Cultivar | S | W | Retention | S | W |
| 'UCR 17-8' | 6.0 b | 6.3 a | 7.2 a | 0.69 a | 0.68 a |
| 'UCRTP6-3' | 6.1 ab | 5.8 ab | 6.8 ab | 0.70 a | 0.65 a |
| 'Bandera' | 5.4 c | 4.9 cd | 6.2 b | 0.65 a | 0.62 a |
| 'Santa Ana' | 6.1 ab | 4.5 d | 5.2 c | 0.68 a | 0.61 a |
| 'TifTuf' | 6.5 a | 5.2 bed | 6.7 ab | 0.69 a | 0.62 a |
| 'Tifway' | 5.9 b | 5.3 bc | 6.9 ab | 0.66 a | 0.64 a |
| Significance | *** | *** | *** | | |

| | DGCI | | Seedhead | Establishment (8 |
|---|---|---|---|---|
| Cultivar | S | W | Production | WAP) |
| 'UCR 17-8' | 0.45 a | 0.45 a | 3.7 b | 94.1 ab |
| 'UCRTP6-3' | 0.46 a | 0.44 a | 2.7 ab | 88.0 ab |
| 'Bandera' | 0.44 a | 0.44 a | 2.5 ab | 98.0 a |
| 'Santa Ana' | 0.45 a | 0.41 a | 3.7 b | 86.4 ab |
| 'TifTuf' | 0.44 a | 0.43 a | 3.0 ab | 96.5 ab |
| 'Tifway' | 0.44 a | 0.44 a | 1.7 a | 68.6 b |
| Significance | | | *** | * |

Means followed by the same letter in a column are not significantly different at P = 0.05
Significance levels: * P < 0.001,  P < 0.01, * P < 0.05, ~P < 0.1.
S = Summer, W = Winter.

TABLE 5

Fairfax, CA 2017-2019

| | Turfgrass Quality | | Winter Retention | NDVI | |
|---|---|---|---|---|---|
| Cultivar | S | W | Color | S | W |
| 'UCR 17-8' | 6.0 ab | 3.9 a | 3.8 ab | 0.72 a | 0.57 ab |
| 'UCRTP6-3' | 5.9 abc | 3.9 a | 4.3 ab | 0.72 a | 0.56 ab |
| 'Bandera' | 5.6 bc | 4.1 a | 4.3 ab | 0.69 ab | 0.58 a |
| 'Santa Ana' | 5.3 c | 4.0 a | 4.3 ab | 0.64 b | 0.50 b |

TABLE 5-continued

| Fairfax, CA 2017-2019 | | | | | |
|---|---|---|---|---|---|
| 'Tiftuf' | 5.9 abc | 4.4 a | 4.9 a | 0.71 a | 0.56 ab |
| 'Tifway' | 6.4 a | 3.4 a | 3.3 b | 0.73 a | 0.55 ab |
| Significance | *** | | | *** | * |

| | DGCI | | Seedhead | Establishment (8 |
|---|---|---|---|---|
| Cultivar | S | W | Production | WAP) |
| 'UCR 17-8' | 0.38 a | 0.41 a | 2.9 a | 44.7 a |
| 'UCRTP6-3' | 0.38 a | 0.41 a | 3.1 a | 27.3 a |
| 'Bandera' | 0.38 a | 0.41 a | 2.4 a | 38.2 a |
| 'Santa Ana' | 0.37 a | 0.40 a | 3.1 a | 24.8 a |
| 'Tiftuf' | 0.37 a | 0.39 a | 4.7 b | 39.3 a |
| 'Tifway' | 0.38 a | 0.39 a | 2.7 a | 16.0 a |
| Significance | | | *** | |

Means followed by the same letter in a column are not significantly different at P = 0.05.
Significance levels: * P < 0.001,  P < 0.01, * P < 0.05, ~P < 0.1.
S = Summer, W = Winter.

TABLE 6

| Riverside, CA 2017-2019 | | | | | |
|---|---|---|---|---|---|
| | Turfgrass Quality | | Winter Color | NDVI | |
| Cultivar | S | W | Retention | S | W |
| 'UCR 17-8' | 6.3 b | 5.5 a | 6.3 ab | 0.72 ab | 0.58 ab |
| 'UCRTP6-3' | 6.7 a | 5.8 a | 6.9 a | 0.73 a | 0.62 a |
| 'Bandera' | 5.7 c | 4.6 c | 5.4 bc | 0.67 c | 0.51 cd |
| 'Santa Ana' | 6 4 ab | 4.7 bc | 4.9 c | 0.71 abc | 0.47 d |
| 'TifTuf' | 6.3 b | 5.6 a | 6.7 a | 0.69 bc | 0.59 ab |
| 'Tifway' | 6.2 b | 5.3 ab | 6.6 a | 0.69 bc | 0.55 bc |
| Significance | *** | *** | *** | *** | *** |

| | DGCI | | Seedhead | Establishment (8 |
|---|---|---|---|---|
| Cultivar | S | W | Production | WAP) |
| 'UCR 17-8' | 0.47 a | 0.43 a | 1.6 a | 66.5 a |
| 'UCRTP6-3' | 0.47 a | 0.42 a | 3.3 ab | 96.8 a |
| 'Bandera' | 0.45 ab | 0.41 a | 3.0 ab | 65.1 a |
| 'Santa Ana' | 0.46 ab | 0.36 b | 2.7 ab | 91.9 a |
| 'TifTuf' | 0.45 b | 0.41 a | 3.9 b | 83.3 a |
| 'Tifway' | 0.45 ab | 0.41 a | 1.7 a | 74.1 a |
| Significance | ** | *** | ** | |

Means followed by the same letter in a column are not significantly different at P = 0.05.
Significance levels: * P < 0.001,  P < 0.01, * P < 0.05, ~P < 0.1.
S = Summer, W = Winter.

To evaluate performance under regular fairway management in Northern California, a study was started in Napa, Calif. in 2019. Plots were established using sod and placed in two fairways. Turfgrass quality in the summer and in the winter (1-9; 9=best), winter color retention (1-9; 9=highest), NDVI (0-1), density (1-9; 9=highest), uniformity (1-9; 9=most uniform) and seedhead production (1-9; 1=no seedheads) were evaluated from 2019 to 2022. Performance of 'UCR 17-8' in comparison to commercial checks and 'UCR TP6-3' is shown in Table 7. 'UCR 17-8' in Napa, Calif. showed high overall quality. In the summer, it was the highest among evaluated entries, comparable only to 'UCR TP6-3' and 'Latitude 36'. In the winter, its quality was similar to 'UCR TP6-3', 'Latitude 36', 'TifTuf', 'Santa Ana', 'Bandera' and 'Tifway II' (not patented), and higher than 'Celebration' and 'Tahoma 31'. Winter color retention of 'UCR 17-8' was higher than of 'Celebration' and 'Tahoma 31', slightly lower than 'Santa Ana' and 'TifTuf', and similar to 'UCR TP6-3', 'Bandera' and 'Latitude 36'. 'UCR 17-8' had dark green genetic color, similar to 'Bandera', 'Tahoma 31', 'UCR TP6-3' and 'Latitude 36'. 'UCR 17-8' had the highest density and uniformity when compared both to commercial checks and to 'UCR TP6-3'. Seedhead production of 'UCR 17-8' was less intensive than most of the evaluated entries, except that of 'Latitude 36' and 'Tahoma 31'. Seedhead production was significantly lower than that of 'Santa Ana' and 'Tifway II'.

TABLE 7

| Fairway Trial, Napa, CA 2019-2022 | | | | | |
|---|---|---|---|---|---|
| | Turfgrass Quality | | Winter Color | Genetic | NDVI |
| Cultivar | S | W | Retention | Color | S |
| 'UCR 17-8' | 7.8 a | 5.4 a | 5.9 ab | 8.3 a | 0.76 a |
| 'UCRTP6-3' | 7.0 ab | 5.3 a | 5.9 ab | 8.2 ab | 0.76 a |
| 'Bandera' | 6.7 bcd | 4.6 ab | 5.2 ab | 8.5 a | 0.73 a |
| 'Celebration' | 4.5 f | 3.2 c | 2.7 d | 6.5 c | 0.66 b |
| 'Latitude 36' | 7.4 ab | 5.2 a | 5.2 ab | 8.2 ab | 0.73 a |
| 'Santa Ana' | 6.7 bc | 5.7 a | 6.3 a | 7.7 abc | 0.75 a |
| 'Tahoma 31 ' | 5.8 de | 3.9 be | 3.7 cd | 8.5 a | 0.70 ab |
| 'TifTuf' | 6.0 cdc | 5.6 a | 6.3 a | 6.7 be | 0.72 ab |
| 'Tifway II' | 5.8 e | 4.9 ab | 4.8 be | 7.5 abc | 0.70 ab |
| Significance | *** | *** | *** | *** | *** |

| | NDVI | | | Seedhead |
|---|---|---|---|---|
| Cultivar | W | Density | Uniformity | Prod. |
| 'UCR 17-8' | 0.57 ab | 8.1 a | 7.8 a | 3.1 a |
| 'UCRTP6-3' | 0.58 ab | 7.6 ab | 6.8 abcd | 4.4 ab |
| 'Bandera' | 0.54 abc | 7.7 ab | 6.9 abcd | 3.6 ab |
| 'Celebration' | 0.41 d | 5.2 c | 5.4 e | 5.3 ab |
| 'Latitude 36' | 0.51 abc | 7.6 ab | 7.4 ab | 3.0 a |
| 'Santa Ana' | 0.60 a | 7.7 ab | 7.2 abc | 5.9 b |
| 'Tahoma 31 ' | 0.45 cd | 6.7 b | 5.8 de | 2.9 a |
| 'TifTuf' | 0.57 ab | 7.4 ab | 6.3 bede | 5.6 ab |
| 'Tifway II' | 0.50 bed | 7.1 ab | 6.1 cde | 5.9 b |
| Significance | *** | *** | ** | *** |

Means followed by the same letter in a column are not significantly different at P = 0.05.
Significance levels: * P < 0.001,  P < 0.01, * P < 0.05, ~P < 0.1.
S = Summer, W = Winter.

'UCR 17-8' was added as local check to 2019 National Turfgrass Evaluation Program ("NTEP") National Bermudagrass Test in Riverside, Calif. Commercial checks in this study were 'Astro' (not patented), 'Latitude 36', 'Tahoma 31', 'TifTuf' and 'Tifway'. The study was planted in June and early July 2019 and was mowed to ⅝ in. Establishment rate (% ground cover), turfgrass quality (1-9; 9=best), spring green-up (1-9; 1=dormant), leaf texture (1-9; 9=finest), genetic color (1-9; 9=darkest green), fall/winter color retention (1-9; 9=highest; starting second full year of the trial) were evaluated. After full establishment was reached, deficit irrigation was applied in the summer of each year (July/August to October) at 35% $ET_0$. During this period turfgrass quality and percent green retention were also evaluated. Data collected between 2019 and spring of 2022, comparing 'UCR 17-8' with commercial cultivars and 'UCR TP6-3' are presented in Table 8. 'UCR 17-8' had good quality under regular irrigation and retained quality well under deficit irrigation. Quality of 'UCR 17-8' under deficit irrigation was comparable to 'TifTuf', 'UCR TP6-3' and 'Tahoma 31', and higher than 'Astro', 'Tifway' and 'Latitude 36'. Green cover retention under deficit irrigation of 'UCR 17-8' was very good, however lower than 'TifTuf'. 'UCR 17-8', 'UCR TP6-3' and 'TifTuf' had the highest fall/winter color retention among analyzed entries, as well as fast spring green-up. 'UCR 17-8' was characterized by dark genetic color, comparable to 'UCR TP6-3', higher than 'Astro', but lower than 'Tahoma 31'.

TABLE 8

2019 NTEP National Bermudagrass Test
Riverside, CA

| | Turfgrass Quality | | Green Cover - Deficit | Fall/ Winter Color Re- | Spring Green- | Gen- | Leaf Tex- |
|---|---|---|---|---|---|---|---|
| Cultiver | R | D | Irrigation | tention | Up | etic Color | ture |
| 'UCR 17-8' | 6.0 a | 5.8 a | 58.5 ab | 7.1 a | 7.1 a | 7.5 ab | 7.0 a |
| 'UCRTP6-3' | 6.0 a | 5.3 ab | 53.8 abc | 7.1 a | 7.1 a | 7.3 ab | 7.0 a |
| 'Astro' | 4.3 c | 4.2 be | 30.3 abc | 4.6 c | 5.0 b | 4.3 c | 5.8b |
| 'Latitude 36' | 4.6 bc | 2.8 c | 17.0 c | 4.7 c | 5.9 ab | 6.2 b | 6.8 a |
| 'Tahoma 31' | 4.8 bc | 4.7 ab | 39.0 abc | 3.2 d | 6.3 ab | 8.2 a | 6.7 ab |
| 'TifTuf' | 6.6 a | 5.7 a | 69.2 a | 7.2 a | 6.9 a | 6.0 b | 6.7 ab |
| 'Tifway' | 5.1 b | 4.2 bc | 25.4 bc | 5.7 b | 6.2 ab | 6.7 ab | 6.5 ab |
| Signi-ficance | *** | *** | ** | *** | ** | *** | ** |

Means followed by the same letter in a column are not significantly different at P = 0.05.
Significance levels: * P < 0.001,  P < 0.01, * P < 0.05, ~P < 0.1.
R = Regular Irrigation; D = Deficit Irrigation.

'UCR 17-8' was included as a local check in the 2018 United States Golf Association ("USGA") National Turfgrass Evaluation Program trial. The trial evaluated performance of warm-season species, including bermudagrass, under three reference evapotranspiration ($ET_0$) replacements: 60%, 45% and 30% $ET_0$. Visual turfgrass quality under regular and deficit irrigation (1-9 scale, 9=best) and percentage green cover under deficit irrigation (using digital image analysis, DIA) were recorded weekly during the deficit irrigation conditions. Recovery, expressed as percentage green cover, was evaluated after regular irrigation was restored. Results for 'UCR 17-8', 'UCR TP6-3' and commercial bermudagrass cultivars are presented in Table 9 and Table 10. At 30% $ET_0$, 'UCR 17-8' retained high quality and green cover, comparable to 'TifTuf' and higher than other cultivars. At 45% $ET_0$, 'UCR 17-8' had the highest quality and green cover among evaluated entries. Under 60% $ET_0$, 'UCR 17-8' also retained high quality, however differences between entries under this $ET_0$ level were less pronounced and no significant differences in green cover were observed. 'UCR 17-8' showed fast recovery. Under 30% and 60% $ET_0$, recovery of 'UCR 17-8' was slower than 'TifTuf', but faster than other cultivars. Under 45% $ET_0$, 'UCR 17-8' had very similar recovery rate to 'TifTuf', higher than all other cultivars. Quality of 'UCR 17-8' in late spring, before deficit irrigation was applied, was the highest in all levels of irrigation. Establishment of 'UCR 17-8' in this trial was comparable to 'Tifway', slower than 'Tahoma 31', 'TifTuf' and 'Premier Pro' (not patented), but faster than 'Dog Tuff' (not patented).

TABLE 9

Turfgrass Quality (TQ) Under Regular and Three Levels of Deficit Irrigation, Turfgrass Quality During Recovery, and Establishment at 8 Weeks After Planting USGA National Turfgrass Evaluation Program, Riverside, CA, 2018-2021

| | TQ - Non-Drought | | | TQ - Drought | | |
|---|---|---|---|---|---|---|
| | Evapotranspiration Replacement ($ET_0$) | | | | | |
| Cultivar | 30% | 45% | 60% | 30% | 45% | 60% |
| 'UCR 17-8' | 3.2 a | 8.4 a | 7.7 a | 4.2 a | 6.1 a | 6.7 ab |
| 'Dog Tuff' | 6.6 bc | 6.6 bc | 6.1 b | 3.6 ab | 4.7 abc | 6.1 ab |
| 'Premier Pro' | 5.8 c | 6.2 c | 7.0 ab | 2.4 b | 3.4 c | 5.4 b |
| 'Tahoma 31' | 6.9 b | 7.3 abc | 7.3 a | 3.1 ab | 4.7 abc | 6.4 ab |
| 'TifTuf' | 7.0 b | 7.1 be | 7.1 a | 4.6 a | 5.4 ab | 6.9 a |
| 'Tifway' | 7.3 ab | 7.7 ab | 7.2 a | 3.6 ab | 4.4 bc | 6.1 ab |
| Significance | *** | * * * | *** | ** | *** | * |

| | TQ - Recovery | | | Establishment (8 WAP) |
|---|---|---|---|---|
| | Evapotranspiration Replacement ($ET_0$) | | | |
| Cultivar | 30% | 45% | 60% | (%) |
| 'UCR 17-8' | 4.1 a | 4.8 ab | 5.3 a | 60.0 b |
| 'Dog Tuff' | 3.5 ab | 3.9 ab | 4.5 a | 42.8 c |
| 'Premier Pro' | 2.1 b | 3.0 b | 4.3 a | 78.8 a |
| 'Tahoma 31' | 3.1 ab | 3.2 b | 4.1 a | 81.9 a |
| 'TifTuf' | 4.4 a | 5.4 a | 5.7 a | 79.0 a |
| 'Tifway' | 4.2 a | 4.3 ab | 4.7 a | 71.5 ab |
| Significance | ** | ** | | *** |

Means followed by the same letter in a column are not significantly different at P=0.05.
Significance levels: * P < 0.001,  P < 0.01, * P < 0.05, ~P < 0.1.

TABLE 10

Green Cover (%) Under Three Levels of Deficit Irrigation and Recovery USGA] National Turfgrass Evaluation Program, Riverside, CA, 2018-2021

| | Green Cover - Drought | | | Green Cover - Recovery | | |
|---|---|---|---|---|---|---|
| | Evapotranspiration Replacement (ETo) | | | | | |
| Cultivar | 30% | 45% | 60% | 30% | 45% | 60% |
| 'UCR 17-8' | 23.2 ab | 62.7 a | 74.1 a | 34 3 ab | 61.5 a | 69.9 ab |
| 'Dog Tuff' | 10.2 ab | 38.0 abc | 66.6 a | 20.9 abc | 33.3 b | 52.7 abc |
| 'Premier Pro' | 3.1 b | 17.1 c | 53.0 a | 3.7 c | 14.5 b | 36.2 c |
| 'Tahoma 31' | 4.7 ab | 33.2 be | 65.2 a | 11.7 bc | 22.4 b | 40.8 bc |
| 'TifTuf' | 24.9 a | 47.4 ab | 75.4 a | 40.5 a | 59.1 a | 80.6 a |
| 'Tifway' | 8.8 ab | 27.2 be | 55.0 a | 28.8 ab | 33.7 b | 53.2 abc |
| Significance | ** | * * * | | *** | *** | *** |

Means followed by the same letter in a column are not significantly different at P = 0.05.
Significance levels: * P < 0.001,  P < 0.01, * P < 0.05, ~P < 0.1.

'UCR 17-8' was tested for prolonged drought tolerance in a field trial in Riverside, Calif., for two years (2020 & 2021) from June to November. Each year, prolonged drought conditions were simulated using two subsequent dry-down periods (60 days; irrigation withheld) followed by recovery periods (14 days; irrigation provided). Plants were evaluated on their performance using measurements of percent living (green) coverage (PC), normalized difference vegetative index (NDVI, 0-1), and overall turf quality (scale of 1 to 9, 9=best). PC was measured on eight separate events per year with digital image analysis (DIA) using the image process ing software ImageJ. Results are presented in Table 11 and Table 12. During the first experimental year, 'UCR 17-8' was found to exhibit a similar mean PC to 'UCR TP6-3', 'Bandera', 'Celebration', 'Santa Ana', 'TifTuf', and 'Tifway II' on all eight events. During the second experimental year, 'UCR 17-8' was found to exhibit a similar mean PC to 'UCR TP6-3', 'Bandera', 'Santa Ana', 'TifTuf', and 'Tifway II' on all eight events; but a lower mean PC than 'Celebration' on 3 events. NDVI was used as a metric to measure overall plant health using a handheld GreenSeeker. During the first experimental year, 'UCR 17-8' was found to exhibit a similar mean NDVI to 'UCR TP6-3', 'Bandera', 'Celebration', 'Santa Ana', 'TifTuf', and 'Tifway II' on all 8 events. During the second experimental year, 'UCR 17-8' was found to exhibit a similar mean NDVI to 'UCR TP6-3', 'Bandera', 'Santa Ana', 'TifTuf', and 'Tifway II' on all eight events; but a lower mean PC than 'Celebration' on two events. Increase of cover observed in second cycle of 2021 resulted from significant rain event (0.2 in).

TABLE 11

Green Cover (%) After 20, 40, and 60 Days Without Irrigation in Riverside, CA

| | Drydown Cycle 1 | | | Recovery |
|---|---|---|---|---|
| Cultivar | 20 d | 40 d | 60 d | Period 1 |
| | | 2020 | | |
| 'UCR 17-8' | 96.5 a | 74.8 a | 39.9 a | 100.0 a |
| 'UCRTP6-3' | 92.4 a | 65.8 a | 30.4 a | 100.0 a |
| 'Bandera' | 72.6 a | 55.2 a | 38.8 a | 100.0 a |
| 'Celebration' | 100.0 a | 100.0 a | 64.8 a | 100.0 a |
| 'Santa Ana' | 98.8 a | 69.0 a | 42.7 a | 100.0 a |
| 'TifTuf' | 98.1 a | 84.5 a | 39.1 a | 100.0 a |
| 'Tifway II' | 85.4 a | 51.6 a | 22.0 a | 96.4 a |
| | | 2021 | | |
| 'UCR 17-8' | 70.2 a | 28.9 a | 3.2 b | 52.2 a |
| 'UCRTP6-3' | 66.5 a | 36.4 a | 5.3 b | 67.6 a |
| 'Bandera' | 41.3 a | 21.8 a | 3.6 b | 45.0 a |
| 'Celebration' | 73.7 a | 66.3 a | 30.6 a | 74.0 a |
| 'Santa Ana' | 64.4 a | 37.6 a | 13.8 ab | 60.3 a |
| 'TifTuf' | 74.9 a | 49.5 a | 13.0 ab | 77.6 a |
| 'Tifway II' | 30.6 a | 11.3 a | 3.0 b | 68.7 a |
| | Drydown Cycle II | | | Recovery |
| Cultivar | 20 d | 40 d | 60 d | Period II |
| | | 2020 | | |
| 'UCR 17-8' | 69.0 ab | 31.1 ab | 23.6 ab | 77.8 ab |
| 'UCRTP6-3' | 72.2 ab | 37.2 ab | 32.0 ab | 71.3 ab |
| 'Bandera' | 52.3 ab | 25.7 ab | 19.6 ab | 52.4 b |
| 'Celebration' | 92.1 ab | 64.2 ab | 58.8 ab | 75.9 ab |
| 'Santa Ana' | 50.4 ab | 25.2 ab | 27.9 ab | 65.0 ab |
| 'TifTuf' | 100.0 a | 80.2 a | 70.7 a | 100.0 a |
| 'Tifway II' | 44.3 b | 15.4 b | 9.1 b | 44.3 b |
| | | 2021 | | |
| 'UCR 17-8' | 9.4 bc | 6.6 b | 8.9 ab | 12.2 ab |
| 'UCRTP6-3' | 18.5 be | 13.1 ab | 22.6 ab | 29.8 ab |
| 'Bandera' | 6.8 be | 5.4 b | 5.6 b | 6.3 b |
| 'Celebration' | 50.9 a | 35.0 ab | 49.8 a | 55.2 a |
| 'Santa Ana' | 22.3 abc | 15.8 ab | 20.1 ab | 26.7 ab |
| 'TifTuf' | 37.1 ab | 21.9 ab | 36.0 ab | 48.5 ab |
| 'Tifway II' | 6.1 c | 4.9 b | 5.4 b | 8.2 b |

Means followed by the same letter in a column are not significantly different at P = 0.05.

TABLE 12

Normalized Difference Vegetation Index (NDVI, 0-1) After 20, 40, and 60 Days Without Irrigation in Riverside, CA

| | Drydown Cycle 1 | | | Recovery |
|---|---|---|---|---|
| Cultivar | 20 d | 40 d | 60 d | Period 1 |
| | | 2020 | | |
| 'UCR 17-8' | 0.63 a | 0.51 a | 0.36 a | 0.75 a |
| 'UCRTP6-3' | 0.64 a | 0.51 a | 0.36 a | 0.81 a |
| 'Bandera' | 0.53 a | 0.44 a | 0.35 a | 0.65 a |
| 'Celebration' | 0.67 a | 0.56 a | 0.43 a | 0.74 a |
| 'Santa Ana' | 0.63 a | 0.49 a | 0.38 a | 0.65 a |
| 'TifTuf' | 0.59 a | 0.47 a | 0.34 a | 0.80 a |
| 'Tifway II' | 0.53 a | 0.41 a | 0.28 a | 0.64 a |
| | | 2021 | | |
| 'UCR 17-8' | 0.55 a | 0.32 a | 0.23 ab | 0.36 a |
| 'UCRTP6-3' | 0.50 a | 0.34 a | 0.27 ab | 0.46 a |
| 'Bandera' | 0.40 a | 0.27 a | 0.23 ab | 0.32 a |
| 'Celebration' | 0.52 a | 0.44 a | 0.39 a | 0.50 a |
| 'Santa Ana' | 0.51 a | 0.36 a | 0.31 ab | 0.43 a |
| 'TifTuf' | 0.54 a | 0 41 a | 0.35 ab | 0.55 a |
| 'Tifway II' | 0.36 a | 0.22 a | 0.20 b | 0.38 a |
| | Drydown Cycle II | | | Recovery |
| Cultivar | 20 d | 40 d | 60 d | Period II |
| | | 2020 | | |
| 'UCR 17-8' | 0.44 a | 0.37 a | 0.35 a | 0.47 a |
| 'UCRTP6-3' | 0.48 a | 0.40 a | 0.39 a | 0.49 a |
| 'Bandera' | 0.36 a | 0.32 a | 0.31 a | 0.35 a |
| 'Celebration' | 0.50 a | 0.45 a | 0.43 a | 0.47 a |
| 'Santa Ana' | 0.37 a | 0.33 a | 0.32 a | 0.45 a |
| 'TifTuf' | 0.55 a | 0.46 a | 0.43 a | 0.57 a |
| 'Tifway II' | 0.36 a | 0.27 a | 0.25 a | 0.36 a |
| | | 2021 | | |
| 'UCR 17-8' | 0.26 ab | 0.20 b | 0.20 ab | 0.19 a |
| 'UCRTP6-3' | 0.32 abc | 0.25 ab | 0.24 ab | 0.24 a |
| 'Bandera' | 0.24 c | 0.20 ab | 0.17 ab | 0.15 a |
| 'Celebration' | 0.40 a | 0.33 a | 0.32 a | 0.34 a |
| 'Santa Ana' | 0.28 abc | 0.27 ab | 0.23 ab | 0.27 a |
| 'TifTuf' | 0.39 ab | 0 31 ab | 0.25 ab | 0.30 a |
| 'Tifway II' | 0.22 c | 0.18 b | 0.16 b | 0.18 a |

Means followed by the same letter in a column are not significantly different at P = 0.05.

When compared to other commercially available bermudagrass cultivars 'UCR 17-8' possesses as good or better winter color retention. 'UCR 17-8' performs exceptionally well under reduced irrigation , comparably only to 'TifTuf'. Overall turf quality characteristics of 'UCR 17-8' are similar to or better than 'TifTuf'.

'UCR 17-8' and 'UCR TP6-3' are genetically similar, sharing the same accessions used in crossing. 'UCR 17-8' is superior in terms of drought resistance, whereas the 'UCR TP6-3' possesses slightly better aesthetic turf quality characteristics. Other differences between the two include a slightly higher seedhead production in 'UCR TP6-3' compared to 'UCR 17-8' in Riverside and Northern California, however lower in the desert. 'UCR 17-8' has better performance under reduced irrigation (35% ET replacement), however 'UCR TP6-3' has better performance and quicker recovery than 'UCR 17-8' when no irrigation is applied. 'UCR 17-8' also has more uniform performance in various locations across California.

I claim:

1. A new and distinct Bermudagrass plant named 'UCR 17-8' substantially as described and illustrated herein.

* * * * *